United States Patent [19]

Mittleman

[11] 4,084,606

[45] Apr. 18, 1978

[54] FLUID TRANSFER DEVICE

[75] Inventor: Herbert Mittleman, Deerfield, Ill.

[73] Assignee: Baxter Travenol Laboratories, Inc., Deerfield, Ill.

[21] Appl. No.: 463,221

[22] Filed: Apr. 23, 1974

[51] Int. Cl.² ............................................. G05d 9/00
[52] U.S. Cl. ........................... 137/102; 128/214 B; 128/274; 137/512.4; 137/846; 137/854; 417/566
[58] Field of Search ............... 137/512, 512.15, 512.4, 137/525, 525.1, 525.3, 102, 854, 846; 128/214 R, 214 B, 274; 417/566; 251/123, 124

[56] References Cited

U.S. PATENT DOCUMENTS

| | | | |
|---|---|---|---|
| 1,514,839 | 11/1924 | Edwards et al. | 251/123 |
| 3,159,176 | 12/1964 | Russell et al. | 137/525.1 |
| 3,572,375 | 3/1971 | Rosenberg | 137/512 |
| 3,730,217 | 5/1973 | Gute | 137/512.4 |

Primary Examiner—Martin P. Schwadron
Assistant Examiner—G. L. Walton
Attorney, Agent, or Firm—George H. Gerstman; Paul C. Flattery; John P. Kirby, Jr.

[57] ABSTRACT

A fluid transfer device is provided for administration of medicament to a patient. The device includes a plastic housing having a first inlet, a second inlet and an outlet, and an umbrella check valve coupling the inlets and outlets. The umbrella check valve is positioned so as to permit flow from the first inlet to the second inlet and from the second inlet to the outlet, but to block flow from the second inlet to the first inlet and from the outlet to both the first inlet and the second inlet.

7 Claims, 7 Drawing Figures

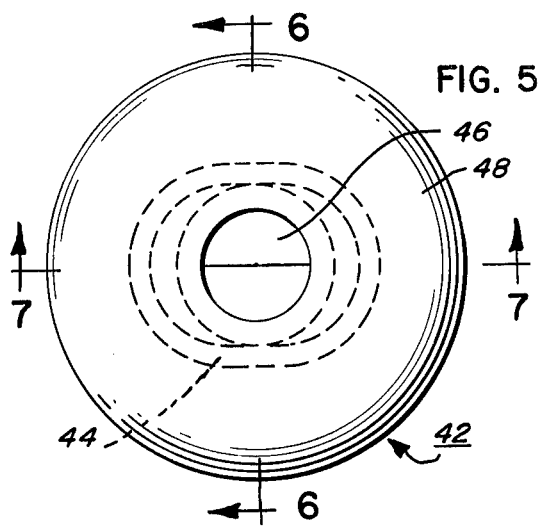
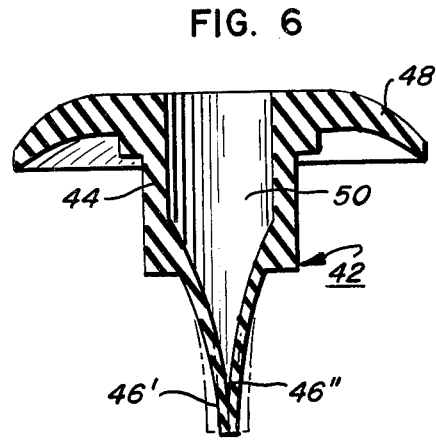
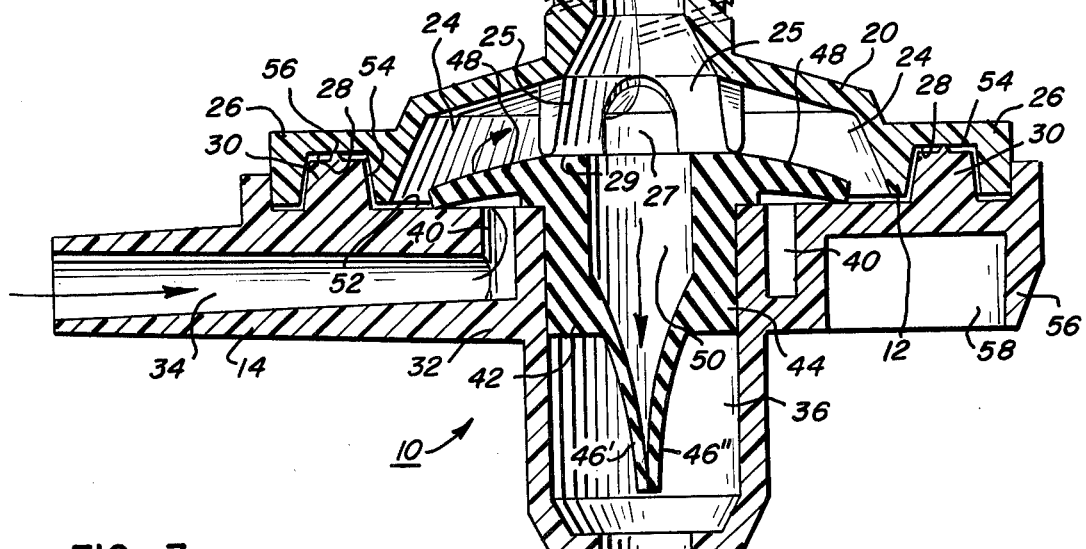
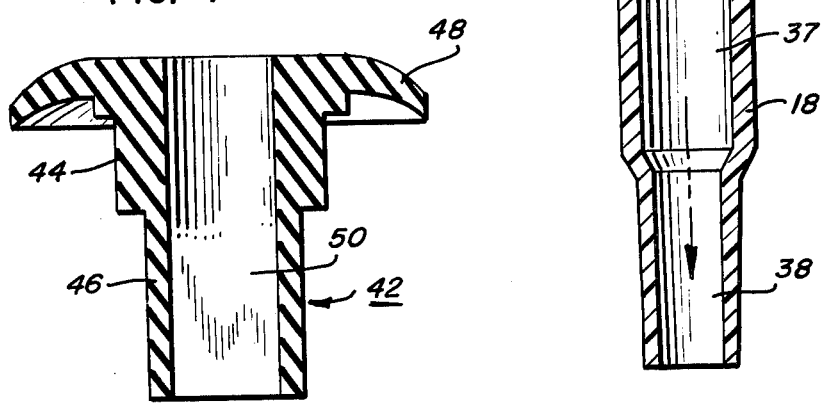

FLUID TRANSFER DEVICE

BACKGROUND OF THE INVENTION

This invention relates to a novel compound valve, and more particularly, to a compound valve which may be utilized in a sterile disposable medicament administration system for administration of medicament to a patient.

In many instances in the medical field, there is a need for a device which can be used as an intermediary for transferring fluid from a first large reservoir to a second smaller reservoir, and from the smaller reservoir to an outlet port. For example, syringes are widely used for injecting fluids into a patient. Occasionally the volume of fluid to be injected is greater than the capacity of the syringe. On such occasions, in order to avoid repeated injections, an intermediary device is utilized to couple the syringe (small reservoir) both to a primary source (large reservoir) and to the patient.

A twin valve T-connector system has been proposed in the prior art for use in the administration of medicaments. Such a system is disclosed in Rosenberg U.S. Pat. Nos. 3,572,375; 3,650,093 and 3,710,942. In a typical use of the Rosenberg twin valve T-connector, a liquid medicament supply is connected to one inlet of the connector and the syringe is connected to the other inlet of the connector. When the plunger of the syringe is withdrawn, the medicament will flow to the syringe and not to the outlet, and when the plunger of the syringe is moved forwardly, the medicament will flow out of the connector via the outlet.

Rosenberg's twin valve T-connector has certain disadvantages. For example, it requires numerous molded parts and its assembly is relatively complex. In addition, two separate valves are required. Further, it is limited to relatively low viscosity fluid and still further, many persons find its appearance distasteful.

It is, therefore, an object of the present invention to provide a fluid transfer device which utilizes a relatively small amount of parts.

Another object of the present invention is to provide a fluid transfer device which is simple in construction and easy to manufacture.

A further object of the present invention is to provide a fluid transfer device which utilizes only a single intermediate valve member, as contrasted to two or more separate intermediate valve members.

Another object of the present invention is to provide a fluid transfer device which permits flow with less pressures than required by prior art devices.

An additional object of the present invention is to provide a fluid transfer device that permits flow of relatively high viscosity fluids.

A still further object of the present invention is to provide a fluid transfer device that is attractive in appearance and is adaptable for simple mounting.

Other objects and advantages of the invention will become apparent as the description proceeds.

BRIEF DESCRIPTION OF THE INVENTION

In accordance with the present invention, there is provided a fluid transfer device which comprises a housing having a first inlet, a second inlet and an outlet. An umbrella check valve couples the first inlet, second inlet and the outlet. The check valve includes a tubular body portion, a resilient normally closed outlet portion and a resilient umbrella portion.

The housing defines a first fluid flow path between the first and second inlets. The housing further defines a second fluid flow path between the second inlet and the outlet. The umbrella check valve is interposed in both the first and second flow paths, with the tubular body portion and the resilient outlet portion being located in the second flow path and the resilient umbrella portion being located in the first flow path.

In this manner, flow is blocked from the outlet to the first and second inlets and is further blocked from the second inlet to the first inlet. On the other hand, flow is permitted from the second inlet to the outlet and from the first inlet to the second inlet.

In an illustrative embodiment of the invention, the housing is partially annular with the first flow path having an annular configuration. The umbrella portion of the check valve is annular and overlies the annular flow path.

In the illustrative embodiment, the check valve is formed of rubber with the tubular body portion being generally elliptical in cross-sectional configuration and being fitted into a generally circular bore.

A more detailed explanation of the invention is provided in the following description and claims, and is illustrated in the accompanying drawings.

BRIEF DESCRIPTION OF THE DRAWINGS

FIG. 4 is a cross-sectional view thereof, taken along the line 4—4 of FIG. 3;

FIG. 5 is a top plan view of the umbrella check valve utilized in connection with the present invention;

FIG. 6 is a cross-section view thereof, taken along the line 6—6 of FIG. 5; and

FIG. 7 is a cross-sectional view thereof, taken along the line 7—7 of FIG. 5.

DETAILED DESCRIPTION OF THE ILLUSTRATIVE EMBODIMENT

Figure 1:
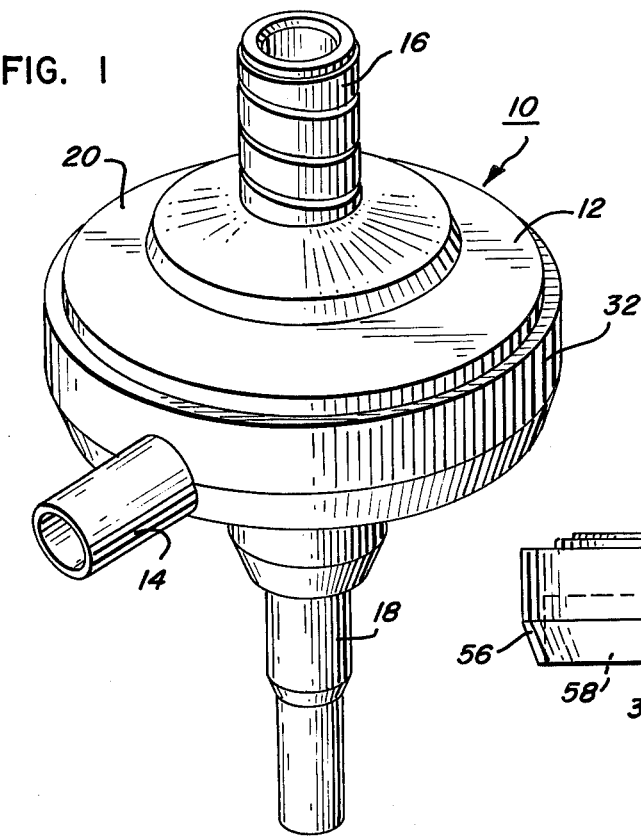
FIG. 1 is a perspective view of a fluid transfer device constructed in accordance with the principles of the present invention.
Figure 2:
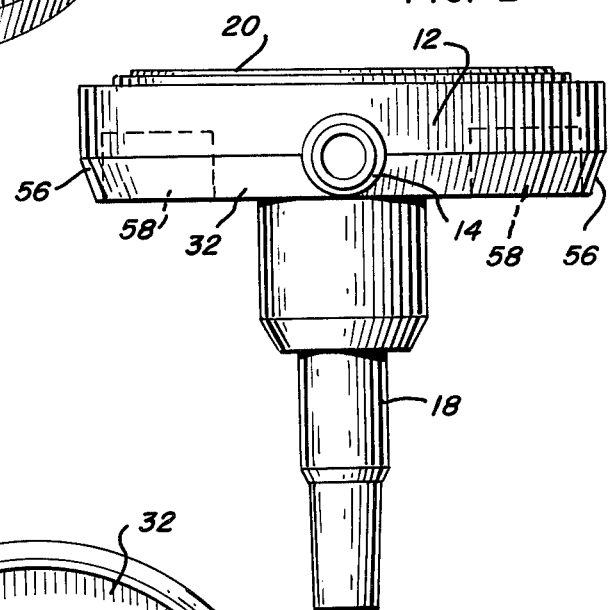
FIG. 2 is a front view thereof.
Figure 3:
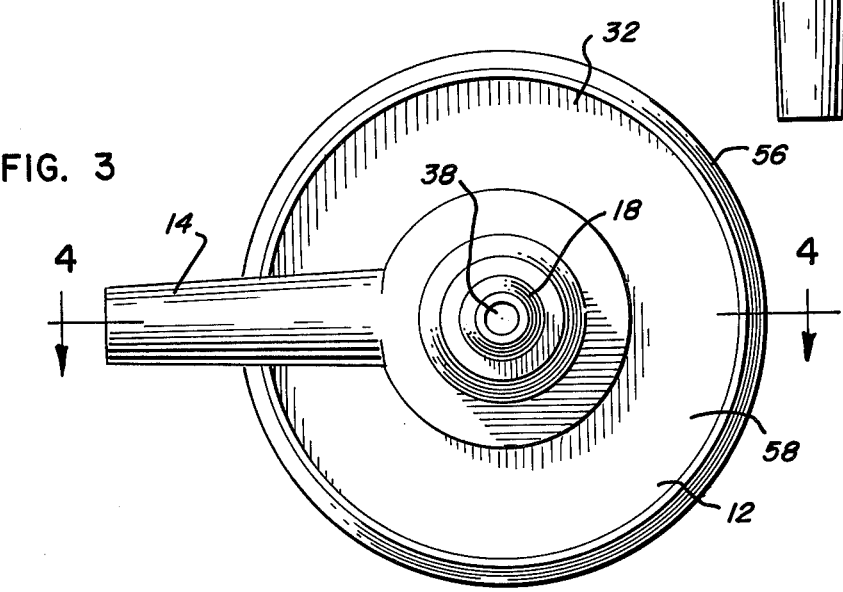
FIG. 3 is a bottom plan view thereof.

Referring first to FIGS. 1 to 4, the fluid transfer device 10 is shown therein including a plastic housing 12, a first inlet 14 at the side of housing 12, a second inlet 16 at the top of housing 12 and an outlet 18 at the bottom of housing 12.

Although housing 12 may be translucent or opaque and formed of various different materials, housing 12 is preferably formed of a clear, plastic material such as polyterephthalate and is molded in two pieces, as shown most clearly in FIG. 4. The top piece 20 includes externally threaded inlet 16 having a bore 22 which communicates with open portion 24. Top member 20 has an annular or circumferential flange 26 which defines an annular groove 28 at its underside. The walls defining groove 28 mate with an upwardly extending annular projection 30 carried by lower member 32. Top member 20 includes downwardly extending fingers 25 which define openings 27 for coupling bore 22 with open portion 24. The underside 29 of fingers 25 rest upon the top of an umbrella check valve which is discussed below.

Lower member 32 includes first inlet 14 defining bore 34 and outlet 18 defining bores 36, 37 and 38, which are in communication with each other but form a tapered outlet path. Bore 34 communicates with annular opening 40 which, when top portion 20 and bottom portion 32 are mated, communicates with open portion 24 except for an interposed umbrella check valve 42.

Check valve 42 can be discerned most readily by referring to FIGS. 4 to 7. The check valve comprises a tubular body portion 44 having a generally elliptical cross-sectional configuration, a resilient outlet portion 46 generally formed of a pair of lips 46', 46" in a generally duckbill configuration, and a resilient, annular umbrella portion 48. Umbrella check valve 42 is preferably formed of rubber and may be latex or synthetic rubber or silicone rubber or plastic having the characteristics of rubber, with a general construction (except for the elliptical body portion) that is similar to that shown in the Russell et al. U.S. Pat. No. 3,159,176. It can be seen that fluid under pressure can flow downwardly via bore 50 of umbrella check valve 42 because lips 46' and 46" will open, but fluid cannot flow upwardly because the lips are normally closed.

Check valve 42 sits snugly within bore 36 due to the fact that body portion 44 is generally elliptical and bore 36 has a generally circular configuration. Annular, flexible umbrella portion 48 overlies annular opening 40 so as to block any downward flow into opening 40. On the other hand, upward flow via bore 34 and annular opening 40 will raise resilient umbrella portion 48 to lift it off wall 52, thereby permitting upward flow into opening 24 and bore 22.

It can be seen that a first fluid path is defined by the housing and includes bore 34, annular opening 40, opening 24, openings 27 and bore 22. A second fluid flow path is defined by the housing and includes bore 22, bore 50 and bores 36, 37 and 38. Check valve 42 is interposed in both fluid flow paths and operates to permit fluid flow from first inlet 14 to second inlet 16 and from second inlet 16 to outlet 18 (when enough pressure is applied to both lips 46', 46"). On the other hand, check valve 42 blocks fluid flow from outlet 18 to inlets 16 and 14 and also blocks fluid flow from inlet 16 to inlet 14.

In the operation of the device, outlet 18 is coupled to a patient by means of suitable tubing, all which is well known in the art. Inlet 14 is coupled to a primary solution of medicament and a pump or syringe is connected to second inlet 16. On the intake stroke of the pump or syringe, the medicament will flow to the pump or syringe via the first flow path and will be held in the pump or syringe until the exhaust stroke. When the exhaust stroke occurs, the fluid within the pump or syringe will be forced downwardly through the second flow path and to the patient.

Top member 20 and bottom member 32 are normally molded so that there is a small space 54 between the portions to be mated, which space is equal to the height of a protuberance 56, as shown in FIG. 4. Top portion 20 and bottom portion 32 are then sonic welded together to provide an attractive, compact and simple unit. Portions 20 and 22 could be bonded by other means, if desired, such as glue, or could be solvent sealed or spin welded.

It is preferred that bottom portion 32 be molded so as to form a downwardly extending circumferential flange 56 defining an opening 58 which extends annularly with respect to bottom portion 32 except for first inlet 14. Annular opening 58 communicates with the outside and opening 58 may be useful to save plastic material, to aid in the molding operation and to form a mounting system.

The illustrative embodiment of the present invention uses only three parts, is simple in construction and easy to manufacture, and is attractive in appearance. Further, because of its unique construction it permits flow with less pressures than required by certain prior art devices and it permits the flow of relative high viscosity fluid.

Although an illustrative embodiment of the invention has been shown and described, it is to be understood that various modifications and substitutions may be made by those skilled in the art without departing from the novel spirit and scope of the present invention.

What is claimed is:

1. A fluid transfer device for the transfer of medical solution which comprises:
   a housing including a first inlet for coupling to the medical solution, a second inlet the axis of which is at an angle with respect to the axis of said first inlet for coupling to pump means, and an outlet;
   said housing defining a first fluid flow path between said first and second inlets;
   said housing defining a second fluid flow path between said second inlet and said outlet;
   an umbrella valve comprising a tubular body portion, a resilient normally closed outlet portion and a resilient umbrella portion;
   said umbrella valve being interposed in both said first and second flow paths;
   said tubular body portion and said resilient outlet portion being located in said second flow path to permit flow under pressure from said second inlet to said outlet but to block flow from said outlet to said first and second inlets, and said resilient umbrella portion being located in said first flow path to permit flow from the first inlet to said second inlet but to block flow from said second inlet to said first inlet;
   means for coupling said second inlet to pump means, said coupling means being constructed to space the pump means from said umbrella portion so that contact between said umbrella portion and the pump means is prevented;
   said housing having an extending member which rests upon said umbrella portion on the side of said umbrella portion that is toward said second inlet.

2. A fluid transfer device as described in claim 1, including means normally closing said resilient outlet portion to prevent fluid flow from said second inlet to said outlet until sufficient pressure is applied to said outlet portion from said second inlet.

3. A fluid transfer device as described in claim 1, said housing being partially annular with a portion of said first flow path having an annular configuration, said umbrella portion of said valve being annular and overlying said annular flow path portion, said first inlet having a cross-sectional area diminishing in the direction of the first flow path for increasing the flow rate from the first inlet to the second inlet.

4. A fluid transfer device as described in claim 1, wherein said resilient outlet portion of said check valve has a duckbill configuration.

5. A fluid transfer device as described in claim 1, wherein said housing is formed of only two parts which are sonic welded together.

6. A fluid transfer device as described in claim 1, wherein said second inlet is externally threaded.

7. A fluid transfer device as described in claim 1, wherein said pump means comprises a syringe and said first inlet and said second inlet are perpendicular.

* * * * *